United States Patent [19]
Yasuda et al.

[11] Patent Number: 5,817,155
[45] Date of Patent: Oct. 6, 1998

[54] EMULSION FOR HAIR TREATMENT

[75] Inventors: Masaaki Yasuda; Yasuhiro Arai; Fumiaki Matsuzaki; Toshio Yanaki; Hideo Nakajima; Michihiro Yamaguchi; Kimio Ohno, all of Yokohama, Japan

[73] Assignee: Shiseido Co., Ltd., Tokyo, Japan

[21] Appl. No.: 761,387

[22] Filed: Dec. 6, 1996

[30] Foreign Application Priority Data

Aug. 8, 1996 [JP] Japan ..................... 8-210149
Aug. 26, 1996 [JP] Japan ..................... 8-223875

[51] Int. Cl.$^6$ ............... A61K 7/06; A61K 7/13
[52] U.S. Cl. ............. 8/406; 8/405; 8/501; 8/94.16; 8/107; 8/111; 424/70.2; 424/70.11; 424/70.13; 452/71
[58] Field of Search ............. 8/405, 406, 415, 8/414, 416, 421, 424, 501, 94.16, 107, 127.51, 110, 111; 424/70.2, 70.5, 70.51, 70.1, 70.11, 70.12, 70.13; 452/71, 81; 252/186.1

[56] References Cited

U.S. PATENT DOCUMENTS

| | | | |
|---|---|---|---|
| 4,555,246 | 11/1985 | Grollier et al. ............... | 8/406 |
| 5,385,674 | 1/1995 | Kupfer et al. .............. | 210/708 |
| 5,693,317 | 12/1997 | Reich et al. ............. | 424/70.15 |

*Primary Examiner*—Alan Diamond
*Attorney, Agent, or Firm*—Townsend & Banta

[57] ABSTRACT

An emulsion for hair treatment is provided which is characterized by the following: the formulation (I) is composed of a W/O type emulsion, which allows the main agent to be stable, and contains preferably an oil soluble polymer compound for the emulsifier; the formulation (I), upon being mixed with formulation (II), can easily undergo demulsification and a phase inversion into an O/W type emulsion; and the emulsion has adequate viscosity to prevent dripping from the hair and a superior dyeing capability. Also, 2-formulation type oxidation hair dye with an excellent hair dyeing effect is provided by adding isostearyl alcohol.

14 Claims, No Drawings

EMULSION FOR HAIR TREATMENT

RELATED APPLICATION

This application claims the priority of Japanese Patent applications No. 8-210149 filed on Aug. 8, 1996 and No. 8-223875 filed on Aug. 26, 1996, which are incorporated herein by reference.

BACKGROUND OF THE INVENTION

1. Field of the Invention

This invention relates in general to an emulsion for hair treatment, and more particularly to a 2-formulation type emulsion for hair treatment which is used as a hair dye, a hair bleach, a permanent wave agent or a depilatory and a method of treating hair using it.

2. The Prior Art

Hair treatment agents such as hair dyes and hair bleaches are required to have an adequate viscosity so that they are retained better and dripping from the hair can be prevented at the time of use. As a result, these hair treatment agents are often prepared as an emulsion.

Conventionally, these emulsions for hair treatment were prepared as an oil-in-water type (hereafter referred to as an O/W type emulsion) because of their ease of preparation and usability. The main agent used in the O/W type emulsion, e.g. a dye in a hair dye and a reducing agent in a permanent wave agent, is usually water soluble and therefore contained in the continuous phase (water phase) which is the outer phase in the emulsion.

However, because of this, such a main agent has increased opportunities to be exposed to the air and therefore has a shortcoming in that it tends to be deteriorated due to oxidation and lacks stability.

BRIEF SUMMARY OF THE INVENTION

The present invention has been developed in view of the aforementioned problem, and its object is to provide a 2-formulation type emulsion for hair treatment which contains a formulation (I) comprising, instead of a conventional O/W type emulsion, a W/O type emulsion which can maintain the stability of the main agent by reducing its exposure to the air wherein formulation (I), upon being mixed with a formulation (II), can easily undergo a phase inversion into an O/W type emulsion and/or demulsification and the emulsion has adequate viscosity to prevent dripping from the hair and superior hair dyeing capabilities.

Another object of the present invention is to provide an oxidation hair dye with a superior hair dyeing effect by adding isostearyl alcohol which enhances the hair dyeing effect.

The inventors conducted earnest research to achieve the aforementioned object and completed the present invention by discovering that the aforementioned problem could be solved by using a formulation (I) which was a W/O type emulsion and contained an oil soluble polymer compound (and polar oil) in its oil phase and a formulation (II) which, when mixed with said formulation (I) at the time of use, caused a phase inversion of said formulation (I) into an oil-in-water type emulsion and/or caused demulsification of said formulation (I).

Furthermore, the inventors conducted earnest research to achieve the aforementioned object and completed the present invention by succeeding in identifying an oil component which enhanced the hair dyeing effect and discovering that an oxidation hair dye with a superior hair dyeing effect could be obtained by adding isostearyl alcohol.

The present invention provides an emulsion for hair treatment comprising a formulation (I) which is a water-in-oil type emulsion and contains the main agent (the active ingredient for the purpose) in the water phase and an emulsifier, preferably an oil soluble polymer compound (and polar oil), in the oil phase and a formulation (II) which, when mixed with said formulation (I), causes a phase inversion of said formulation (I) into an oil-in-water type emulsion and/or causes demulsification of said formulation (I) as well as a hair treatment method using this emulsion.

Also, the present invention provides a 2-formulation type oxidation hair dye comprising a formulation (I) which contains an oxidation dye and a formulation (II) which contains an oxidizing agent wherein they are mixed together before use.

DETAILED DESCRIPTION

The present invention is described in detail below.

According to the present invention, the main agent, when in storage, is contained in the inner phase of the W/O type emulsion and free from oxidation by the air, resulting in a higher stability of the main agent. Also, since ingredients such as alkali agents are contained in the inner phase, it is possible to prevent corrosion and such of the container and reduce offensive odors. Furthermore, since lipophilic perfumes are contained in the oil phase, which is the outer phase, the fragrance of the perfumes can be observed more easily.

When preparing the emulsion for hair treatment which uses the W/O type emulsion of the present invention for formulation (I), the adjustment of the viscosity is sometimes difficult depending on the ingredients contained. For example, if a large amount of surfactant is used to improve the stability of the emulsion, then it is difficult to maintain an adequate viscosity to prevent dripping from the hair at the time of mixing with formulation (II). Also, there is a problem in that some of the emulsions for hair treatment which use a W/O type emulsion have inadequate hair dyeing capabilities. These problems can be solved by using an oil soluble polymer compound for the emulsifier and adding polar oil, particularly isostearyl alcohol, to enhance the effect of the main agent, i.e. the dye. Furthermore, at the time of application to the hair, an adequate viscosity is maintained and dripping can be prevented.

The emulsion for hair treatment according to the present invention can be used for various purposes. It can be used as, for example, a hair dye, a hair bleach, a permanent wave agent, a depilatory, etc. Examples of the main agent for the hair dye include oxidation dyes such as p-diamines which have one or more types of $NH_2$-group, $NHR_1$-group or $N(R_1)_2$-group ($R_1$ is an alkyl or hydroxyalkyl group with a carbon number of 1–4) such as p-phenylenediamine, p-toluenediamine, N-methyl-p-phenylenediamine, N,N-dimethyl-p-phenylenediamine, N,N-diethyl-2-methyl-p-phenylenediamine, N-ethyl-N-(hydroxyethyl)-p-phenylenediamine, chloro-p-phenylenediamine, N, N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-(2-methoxyethyl)-p-phenylenediamine; 2,5-diaminopyridine derivatives; p-aminophenols such as paraaminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,4-diaminophenol and 5-aminosalicylic acid, o-aminophenols, o-phenylenediamines, α-naphtol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, hydroquinone, 2,4-diaminoanisole, m-toluenediamine, 4-aminophenol, resorcinol, resorcinolmonomethyl ether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxy-2-chinolon, m-aminophenol, 4-chlororesorcinol, 2-methylresorcinol, 2,4-diaminophenoxyethanol, 3,5-diamino-trifluoromethylbenzene, 2,4-diamino-fluorobenzene, 3,5-diamino-fluorobenzene, 2,4-diamino-6-dihydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 2,6-diaminopyrimidine, as well as 2-amino-4-nitrophenol, 2-amino-5-nitrophenol, nitro-p-phenylenediamine hydrochloride, nitro-p-phenylenediamine, p-aminophenylsulfamic acid, p-nitro-o-phenylenediamine, picramic acid, sodium picramate, picric acid, chrome brown RH, hematin, nitro-p-phenylenediamine sulfate salt, p-nitro-o-phenylenediamine sulfate, p-nitro-m-phenylenediamine sulfate, 1-amino-4-methylaminoanthraquinone and 1,4-diaminoanthraquinone; and also direct dyes including acidic dyes such as red 2, red 3, red 102, red 04, red 105, red 106, yellow 4, yellow 5, green 3, blue 1, blue 2, red 201, red 227, red 230, red 231, red 232, orange 205, orange 207, yellow 202, yellow 203, green 201, green 204, green 205, blue 202, blue 203, blue 205, brown 201, red 401, red 502, red 503, red 504, red 506, orange 402, yellow 402, yellow 403, yellow 406, yellow 407, green 401, green 402, violet 401 and black 401; oil soluble dyes including red 215, red 218, red 225, orange 201, orange 206, yellow 201, yellow 204, green 202, violet 201, red 501, red 505, orange 403, yellow 404, yellow 405 and blue 403; basic dyes such as red 213 and red 214; and basic dyes from Arianor, Inc. such as Sienna Brown, Mahogany, Madder Red, Steel Blue and Straw Yellow. Examples of the main agent for the bleach are oxidizing agents such as hydrogen peroxide and bromate. Examples of the main agent for the permanent wave agent and the depilatory are reducing agents such as thioglycolic acid, thiogylcolate, cysteine, glyceryl thioglycolate, thioglycerine, cysteamine thiosulfate, thiolactic acid and thiolactate. Selection of those main agents is not limited in particular as long as it is hydrophilic and distributed more to the water phase.

In the W/O type emulsion (formulation (I)) of the present invention, the oil phase components are not limited in particular, and hydrocarbons, oil/fats, wax, higher fatty acids, higher fatty alcohols, ester oils, silicones, etc. can be used.

In the W/O type emulsion (formulation (I)) of the present invention, examples of the polar oil added to the oil phase include ester oils such as isopropyl myristate, cetyl octanoate, octyldodecyl iyristate, isopropyl palmitate, butyl stearate, hexyl laurate, myristyl myristate, decyl oleate, hexyldecyl dimethyloctanoate, cetyl lactate, myristyl lactate, lanoline acetate, isocetyl stearate, isocetyl isostearate, cholesteryl 12-hydroxystearate, dipentaerythritol fatty acid ester, N-alkylglycol monoisostearate, neopentylglycol dicaprate, isostearyl malate, di-2-ethylhexyl sebacate, di-2-hexyldecyl myristate, di-2-hexyldecyl palmitate, di-2-hexyldecyl adipate, diisopropyl sebacate, 2-ethylhexyl succinate, ethyl acetate, butyl acetate, amyl acetate and triethyl citrate, and higher alcohol such as lauryl alcohol, oetyl alcohol, stearyl alcohol, behenyl alcohol, myristyl alcohol, oleyl alcohol, cetostearyl alcohol, batyl alcohol, 2-decyltetradecinol, lanoline alcohol, cholesterol, phytosterol, hexyldodecanol, isostearyl alcohol and octyldodecanol. Particularly preferable are higher alcohols which are in a liquid state at ordinary temperatures, such as oleyl alcohol, isostearyl alcohol and octyldodecanol. The most preferable is to add isostearyl alcohol to the oil phase. As for other oil components, hydrocarbons, oil/fats, fatty acids and silicones can be added in any amount as long as the emulsion stability is not affected.

For the emulsifier used to prepare the W/O type emulsion of the present invention, those which generally used for preparation of an emulsion such as one or more types of surfactant, organic modified clay minerals and oil soluble polymer compound can be used in the oil phase. Particularly preferable is an oil soluble polymer compound and ethyl cellulose is the most preferable in the present invention.

When using a surfactant, for example, for the emulsifier, commonly used anionic surfactants, cationic surfactants, amphoteric surfactants and non-ionic surfactants can be used.

When using a surfactant for the emulsifier for manufacturing the W/O type emulsion of the present invention, it is preferable to use those with a HLB value in the range of 1–12. When two or more surfactants are mixed for use, it is preferable to have a mixed HLB value in the range of 1–12. In addition to the aforementioned surfactants, it is possible to add amino acids and their salts such as glutamic acid and aspartic acid, polyhydric alcohol such as polyethylene glycol, and inorganic salts such as sodium sulfate for stabilization. By doing this, a W/O type emulsion with a superior stability can be obtained efficiently.

The organic modified clay mineral which can be used as the emulsifier for manufacturing the W/O type emulsion of the present invention can be obtained by, for example, the following methods: as described in Japanese unexamined patent publication Tokkai Sho 61-129033 and Tokkai Sho 61-245836, water-induced-swelling clay minerals, a quarternary ammonium salt type cationic surfactant and a non-ionic surfactant are dispersed and stirred in a solvent with a low boiling point such as water, acetone or a lower alcohol; or, water-induced-swelling clay minerals and a quarternary ammonium salt type cationic surfactant are treated in a solvent with a low boiling point to obtain cation modified clay minerals, which are then treated with a non-ionic surfactant, followed by removal of the solvent with a low boiling point.

By using organic modified clay minerals for the emulsifier, it is possible to efficiently obtain an emulsion with superior stability without high temperature heating. Therefore, when preparing an emulsion containing a substance which is unstable with heat, such as oxidation dyes, and/or highly volatile alkaline agents such as ammonia, it is preferable to use organic modified clay minerals for the emulsifier.

In the present invention, when using an oil soluble polymer compound for the emulsifier, ethyl cellulose, ethylhydroxyethyl cellulose, nitro cellulose, polyvinyl acetate, polymethylmethacrylate, etc. can be used.

In the W/O type emulsion of the present invention, preferable embodiments of the oil soluble polymer compound added to the oil phase include a cellulose ether or a mixture of them. An ethyl cellulose with ethoxy substitution on one or more of its hydroxyl groups is preferable. Depending on the recipe, one or multiple types of cellulose ethers with different substitution ratios and molecular weights can be used.

Also, in the W/O type emulsion of the present invention, a water soluble polymer compound can be added to the water phase. Examples of such a water soluble polymer compound include water soluble polymer compounds commonly used in cosmetics. Preferable are carboxymethyl cellulose, hydroxyethyl cellulose, hydroxypropyl cellulose and cationized cellulose. By adding these, the viscosity of the emulsion of the present invention can be improved.

The W/O type emulsion of formulation (I) of the present invention can be prepared using a conventional emulsification method. For example, it can be prepared by mixing the aforementioned ingredients and the water phase ingredients and giving the mixture mechanical energy from the outside by means of a homogenizer, mixer, colloid mill, etc.

There are various examples of formulation (II) of the emulsion for hair treatment of the present invention, depending on the composition of the formulation (I). For example, if the formulation (I) is a W/O type emulsion which contains water with an inner phase ratio near saturation, formulation (II) can cause phase inversion or/and demulsification of the formulation (I) if it has more than a certain amount of water.

Also, W/O type emulsions are generally unstable when exposed to lower alcohols such as ethanol and isopropyl alcohol, inorganic salts with the salt effect such as sodium bisulfite and hydrophilic surfactants with a HLB value of 12 or more. When mixed with these, the W/O type emulsions are known to undergo phase inversion or/and demulsification. Therefore, anything that contains these substances at a concentration higher than the prescribed value can be used as formulation (II) regardless of the form, i.e. liquid, gel, cream, etc.

The mixing ratio of the formulation (I) and formulation (II) is not limited in particular as long as it allows phase inversion or/and demulsification of the formulation (I) and does not affect the effect of the main agent contained in the formulation (I). In the present invention, other ingredients used in common hair treatment agents such as perfumes, pH control agents, aromatic alcohols, preservatives, humectants, water soluble thickeners, ultraviolet light absorbents, sequestering agents, etc. can be added to the W/O type emulsion (the formulation (I)) or formulation (II), or both, as long as the effect of the present invention is not affected.

A 2-formulation type hair dye which contains an oxidation dye is described below as a hair treatment agent according to the present invention.

This 2-formulation type hair dye comprises a formulation (I) which is a W/O type emulsion and contains an oxidation dye which develops a color through oxidation and a formulation (II) which contains an oxidizing agent such as hydrogen peroxide. Since such a 2-formulation type hair dye contains the oxidation dye in the water phase, which is the inner phase, the dye is free from exposure to the air and deterioration of the hair dye is controlled even after prolonged storage, resulting in a hair dye with a good stability.

When using the hair treatment agent according to the present invention as a hair dye, it is also possible to use a direct dye which has a color from the beginning. The hair dyeing effect can be obtained by adding a prescribed amount of a direct dye such as a tar pigment or nitro dye. Furthermore, in the W/O type formulation (I) of said 2-formulation type oxidation hair dye, if a small amount of the aforementioned direct dye is added in addition to the oxidation dye, then there is no prominent color development when the formulation (I) is by itself because the direct dye is contained in the dispersion phase (inner phase). However, when the formulation (I) undergoes phase inversion and/or demulsification upon being mixed with formulation (II), the direct dye comes out to the continuous phase and prominent color development can be seen. Since this phenomenon indicates that the mixing of the formulation (I) and formulation (II) is complete and the phase inversion and/or demulsification of the formulation (I) has taken place, it can be used as an indicator of the completion of the mixing when the 2-formulation type hair dye of the present invention is used.

In the 2-formulation type hair dye of the present invention, it is possible to enhance the hair dyeing effect by adding isostearyl alcohol, regardless of the formulation of the W/O type emulsion and such.

EXAMPLES

Examples of the present invention are described below. The present invention is not limited to these examples. The amount of each ingredient is indicated in weight percent units.

Examples 1-1 through 1-9

"Preparation of the W/O type emulsion for hair treatment (the formulation (I))"

For the W/O type emulsion for hair treatment of the present invention, a W/O type emulsion with an oxidation dye as the main agent was prepared.

Specifically, following the recipes shown in Table 1, the water phase containing aqueous ingredients was added to the oil phase containing the oil soluble polymer compound (emulsifier: ethyl cellulose) and a polar oil, and the mixture was emulsified to prepare the W/O type emulsions 1-1 through 1-5. For Examples 1-6 through 1-9, a surfactant or organic modified clay minerals is used for the emulsifier and a conventional method was employed to obtain the W/O type emulsions.

TABLE 1

|  | Example 1-1 | Example 1-2 | Example 1-3 | Example 1-4 | Example 1-5 | Example 1-6 | Example 1-7 | Example 1-8 | Example 1-9 |
| --- | --- | --- | --- | --- | --- | --- | --- | --- | --- |
| Ethyl cellulose (N-4 from Hercules, Inc.) | 0.25 | 1.0 | — | — | — | — | — | — | — |
| Ethyl cellulose (N-22 from Hercules, Inc.) | — | — | 0.5 | 0.5 | — | — | — | — | — |
| Ethyl cellulose (N-50 from Hercules, Inc.) | — | — | — | — | 0.75 | — | — | — | — |

TABLE 1-continued

|  | Example 1-1 | Example 1-2 | Example 1-3 | Example 1-4 | Example 1-5 | Example 1-6 | Example 1-7 | Example 1-8 | Example 1-9 |
| --- | --- | --- | --- | --- | --- | --- | --- | --- | --- |
| Ethanol | — | 1.0 | 2.0 | 0.5 | 2.0 | — | — | — | — |
| Octyldodecanol | 15.0 | 5.0 | 5.0 | — | 5.0 | — | — | — | 5.0 |
| Isostearyl alcohol | — | 10.0 | 10.0 | 5.0 | 15.0 | 5.0 | 5.0 | 5.0 | — |
| Octyldodecyl myristate | 5.0 | — | 5.0 | — | 5.0 | — | — | — | — |
| Isopropyl myristate | — | 5.0 | — | — | 5.0 | — | — | — | — |
| Methylphenyl polysiloxane | — | 5.0 | — | 15.0 | 5.0 | 15.0 | — | 15.0 | — |
| Liquid paraffin | — | — | — | — | — | — | 20.0 | — | 25.0 |
| POE (3) oleyl ether | 0.5 | 0.5 | — | — | — | 5.0 | 5.0 | — | — |
| Organic modified clay mineral (Benzyldimethyl stearyl ammonium chloride treated hectorite (Benton 38)) | — | — | — | — | — | — | — | 1.0 | 1.0 |
| Polyethylene glycol dioleate | — | — | — | — | — | — | — | 0.2 | 0.2 |
| Cationized cellulose | 0.5 | — | 1.0 | — | 0.5 | — | — | — | — |
| Carboxymethyl cellulose | — | — | — | 0.5 | — | 0.5 | 0.5 | 0.5 | 0.5 |
| Glycerine | — | 5.0 | — | 5.0 | 5.0 | 5.0 | 5.0 | 5.0 | 5.0 |
| p-phenylenediamine | 0.5 | 0.5 | 0.5 | 0.5 | 0.5 | 0.5 | 0.5 | 0.5 | 0.5 |
| Resorcinol | 0.1 | 0.1 | 0.1 | 0.1 | 0.1 | 0.1 | 0.1 | 0.1 | 0.1 |
| Monoethanolamine | 1.0 | 1.0 | 1.0 | 1.0 | 1.0 | 1.0 | 1.0 | 1.0 | 1.0 |
| Aqueous ammonia | 3.0 | 3.0 | 3.0 | 3.0 | 3.0 | 3.0 | 3.0 | 3.0 | 3.0 |
| Chelating agent, preservative | Appropriate amount | | | | | | | | |
| Stabilizer | Appropriate amount | | | | | | | | |
| Perfume | Appropriate amount | | | | | | | | |
| Purified water | Appropriate amount | | | | | | | | |

"Preparation of formulation (II)"

Following the recipes shown in Table 2, formulation (II) of the hair treatment agent according to the present invention was prepared.

TABLE 2

|  | Example 2-1 | Example 2-2 | Example 2-3 |
| --- | --- | --- | --- |
| Aqueous hydrogen peroxide (30%) | 20.0 | 20.0 | 20.0 |
| Ethanol | — | 30.0 | — |
| Cetostearyl alcohol | — | — | 5.0 |
| Sodium laurylsulfate | — | — | 0.5 |
| POE (20) cetyl ether | — | — | 0.5 |
| pH control agent | Appropriate amount | | |
| Preservative | Appropriate amount | | |
| Purified water | Appropriate amount | | |
| pH | 2.5 | 4.0 | 2.5 |

"Stability of the formulation (I)"

A stability test of the W/O type emulsions of Examples 1-1 through 1-9 was conducted and stability after 1 week and after 4 weeks was evaluated using the following standard.

○: No change in external appearance; stable.

X: Oil separation and/or separation of water is observed.

The results are shown in Table 3.

TABLE 3

| Example | 1-1 | 1-2 | 1-3 | 1-4 | 1-5 | 1-6 | 1-7 | 1-8 | 1-9 |
| --- | --- | --- | --- | --- | --- | --- | --- | --- | --- |
| After 1 week | ○ | ○ | ○ | ○ | ○ | ○ | ○ | ○ | ○ |
| After 4 weeks | ○ | ○ | ○ | ○ | ○ | X | ○ | X | ○ |

As clearly shown in Table 3, the W/O type emulsions of Examples 1-1 through 1-9 were stable after 1 week at 50° C. The W/O type emulsions of Examples 1-1 through 1-5 were stable after 4 week at 50° C., whereas the W/O type emulsions of Examples 1-6 and 1-8 were unstable.

For a Comparative example, an O/W type emulsion with the following composition was prepared using a conventional method and let stand for 1 week at 50° C. As a result the oxidation dye developed a color.

The reason for this is believed to be as follows: the oxidation dye in the W/O type emulsion of Example 1-9 is contained in the water phase, which is the inner phase, and therefore almost no oxidation by the air took place, whereas the oxidation dye in the O/W type emulsion of the Comparative example is contained in the water phase, which is the outer phase, and therefore oxidation by the air did take place.

<Comparative example: O/W type emulsion>

| Liquid paraffin | 5.0 |
| --- | --- |
| Cetyl alcohol | 10.0 |
| POE (20) oleyl ether | 3.0 |
| 1,3 butylene glycol | 5.0 |
| Paraphenylenediamine | 0.5 |
| Monoethanolamine | 1.0 |
| Aqueous ammonia (28%) | 3.0 |
| Resorcinol | 0.1 |
| Chelating agent and preservative | Appropriate amount |
| Perfume | Appropriate amount |
| Purified water | Balance |

"A phase inversion and/or demulsification test and a dyeing test of the mixture of the formulation (I) and formulation (II)"

The W/O type emulsions of Examples 1-1 through 1-5, which showed good stability, were mixed with equal amounts of formulation (II)s from Examples 2-1 through 2-3 and it was determined whether or not phase inversion to the O/W type and/or demulsification occurred. The evaluation was made based on dilutability in water. Also, for the combinations for which phase inversion or/and demulsification occurred, a dyeing test using human hair was conducted, and, at the time of application, it was determined whether or not dripping of the hair dye from the hair occurred.

The results are shown in Table 4.

TABLE 4

| Formulation (II) | Formulation (I) | | | | |
|---|---|---|---|---|---|
| | Example 1-1 | Example 1-2 | Example 1-3 | Example 1-4 | Example 1-5 |
| Example 2-1 | o | x | x | x | x |
| | o | — | — | — | — |
| Example 2-2 | o | o | x | x | x |
| | o | o | — | — | — |
| Example 2-3 | o | o | o | o | o |
| | o | o | o | o | o |

Upper row;
o: Phase inversion/demulsification occurred.
x: Phase inversion/demulsification did not occur.
Lower row;
o: No dripping from the hair.
x: Dripping was observed.

As clearly shown in Table 4, all of the W/O type emulsions of Examples 1-1 through 1-5 underwent phase inversion and/or demulsification and none of them dripped from the hair.

The following are examples of the formulation (I) with active ingredients added as appropriate for their various purposes.

Example 2

| | |
|---|---|
| Ethyl cellulose | 0.5 |
| (N-22 from Hercules, Inc.) | |
| Ethanol | 1.0 |
| Isostearyl alcohol | 5.0 |
| Octyl palmitate | 5.0 |
| Methylphenyl polysiloxane | 10.0 |
| Monoethanolamine | 2.0 |
| Aqueous ammonia (28%) | 5.0 |
| Hydrolyzed collagen protein | 0.5 |
| EDTA salt | 0.2 |
| L-ascorbic acid | 0.5 |
| Sodium hydrosulfite | 0.1 |
| Paraphenylenediamine | 1.0 |
| Resorcinol | 0.5 |
| Orthoaminophenol | 0.2 |
| Perfume | Appropriate amount |
| Purified water | Balance |

Example 3

| | |
|---|---|
| Ethyl cellulose | 0.3 |
| (N-22 from Hercules, Inc.) | |
| Ethanol | 2.0 |
| Isostearyl alcohol | 5.0 |
| Octyl dodecanol | 3.0 |
| Octyl palmitate | 5.0 |
| Methylphenyl polysiloxane | 5.0 |
| Monoethanolamine | 1.0 |
| Aqueous ammonia (28%) | 3.0 |
| Amodimethycone | 1.0 |
| (SM-8702C from Toray Silicone Co. Ltd.) | |
| EDTA salt | 0.2 |
| L-ascorbic acid | 0.5 |
| Ammonium thioglycolate solution (50%) | 1.0 |
| Paraphenylenediamine | 0.5 |
| Resorcinol | 0.2 |
| Metaaminophenol | 0.1 |
| Perfume | Appropriate amount |
| Purified water | Balance |

Example 4

| | |
|---|---|
| Ethyl cellulose | 0.5 |
| (N-7 from Hercules, Inc.) | |
| Ethanol | 0.5 |
| Isostearyl alcohol | 10.0 |
| Octyl dodecanol | 3.0 |
| Octyl palmitate | 5.0 |
| Sodium hydroxide | 1.0 |
| Monoethanolamine | 3.0 |
| Hydrolyzed keratin protein | 0.3 |
| Amodimethycone | 1.0 |
| (APS-10-DMS from Shin-Etsu Chemical Co., Ltd.) | |
| EDTA salt | 0.2 |
| L-ascorbic acid | 0.5 |
| Sodium hydrosulfite | 0.1 |
| Paraphenylenediamine | 1.0 |
| Orthoaminophenol | 0.5 |
| Perfume | Appropriate amount |
| Purified water | Balance |

Example 5

| | |
|---|---|
| Ethly cellulose | 0.5 |
| (N-22 from Hercules, Inc.) | |
| Ethanol | 1.0 |
| Isostearyl alcohol | 5.0 |
| Methylphenyl polysiloxane | 15.0 |
| Monoethanolamine | 2.0 |
| Aqueous ammonia (28%) | 6.0 |
| EDTA salt | 1.0 |
| L-ascorbic acid | 0.5 |
| Sodium hydrosulfite | 0.5 |
| Hydrolyzed quarternarized collagen protein | 1.0 |
| Amodimethycone | 2.0 |
| (SM-8702C from Toray Silicone Co. Ltd.) | |
| Paraphenylenediamine | 1.0 |
| Resorcinol | 1.2 |
| Metaphenylenediamine | 0.3 |
| Perfume | Appropriate amount |
| Purified water | Balance |

Example 6

| | |
|---|---|
| Ethyl cellulose | 1.0 |
| (N-4 from Hercules, Inc.) | |
| Isostearyl alcohol | 10.0 |
| Octyldodecanol | 5.0 |
| Dimethyl polysiloxane | 0.2 |
| (Degree of polymerization: 3,000–6,000) | |
| Dimethyl polysiloxane 6 cs | 2.0 |
| Monoethanolamine | 1.0 |
| Aqueous ammonia (28%) | 5.0 |
| EDTA salt | 0.5 |
| L-ascorbic acid | 0.5 |
| Ammonium thioglycolate (50%) | 1.0 |
| Paraphenylenediamine | 1.0 |
| Resorcinol | 0.5 |
| Metaaminophenol | 0.3 |
| Perfume | Appropriate amount |
| Purified water | Balance |

Example 7

| | |
|---|---|
| Ethyl cellulose | 0.2 |
| (N-50 from Hercules, Inc.) | |
| Ethanol | 0.5 |
| Isostearyl alcohol | 10.0 |
| Octyl dodecanol | 7.0 |
| Octyl palmitate | 10.0 |
| Dimethyl siloxane/methyl (polyoxyethylene) siloxane copolymer (SC-9450 from Toray Silicone Co. Ltd.) | 2.0 |
| Hydroxyethanediphosphonic acid (60%) | 1.0 |
| Monoethanolamine | 2.0 |
| L-ascorbic acid | 0.5 |
| Sodium hydrosulfite | 0.1 |
| Paraphenylenediamine | 0.5 |
| Orthoaminophenol | 0.5 |
| Perfume | Appropriate amount |
| Purified water | Balance |

Example 8

| | |
|---|---|
| Ethyl cellulose | 0.25 |
| (N-4 from Hercules, Inc.) | |
| Ethanol | 1.0 |
| Isostearyl alcohol | 5.0 |
| Isoparaffin | 15.0 |
| Monoethanolamine | 2.0 |
| Ammonium carbonate | 5.0 |
| Aqueous ammonia (28%) | 5.0 |
| EDTA salt | 0.5 |
| Pyrolidone carboxylate salt | 0.5 |
| L-ascorbic acid | 0.5 |
| Ammonium thioglycolate (50%) | 1.0 |
| Paraphenylenediamine | 0.5 |
| Resorcinol | 0.2 |
| Paranitroorthophenylenediamine | O.3 |
| Perfume | Appropriate amount |
| Purified water | Balance |

Example 9

| | |
|---|---|
| Ethyl cellulose | 1.0 |
| (N-22 from Hercules, Inc.) | |
| Benzyl alcohol | 5.0 |
| Isostearyl alcohol | 5.0 |
| Methylphenyl polysiloxane | 20.0 |
| Monoethanolamine | 2.0 |
| Aqueous ammonia (28%) | 5.0 |
| EDTA salt | 0.5 |
| N-methyl pyrolidone | 5.0 |
| L-ascorbic acid | 0.5 |
| Sodium hydrosulfite | 0.2 |
| Paratoluenediamine sulfate | 2.5 |
| Resorcinol | 1.0 |
| Metaaminophenol | 0.3 |
| Paraaminophenol | 0.3 |
| Perfume | Appropriate amount |
| Purified water | Balance |

Each of the examples shown here was an emulsion for hair treatment which had superior stability of the main agent and a superior hair dyeing effect and caused no dripping from the hair during use.

The effect of the present invention was clearly shown in these results as well.

Examples of 2-formulation type oxidation hair dyes containing isostearyl alcohol are shown below. In examples and comparative examples, "%" always means "wt %".

Examples 10–12
Reference Rest, Comparative Examples 1–2

(Dyeing test)

10 g of formulation (I) and 10 g of formulation (II) were thoroughly mixed together and a 4 cm×4 cm piece of JIS wool white cloth was soaked in the mixture. After incubating for 30 minutes at room temperature, the wool cloth was thoroughly rinsed in warm water and dried. Pieces of wool cloth from the Examples and Comparative examples were compared with the wool cloth of the reference test by means of visual observation.

⊚: Dyed much better than the wool cloth of the reference test.

○: Dyed better than the wool cloth of the reference test.

Δ: Dyed to the same degree as the reference test.

X: Dyed poorly compared with the wool cloth of the reference test.

(Preparation of the hair dye composition)

Using the samples listed in Table 5, preparation was carried out according to the following recipes with a conventional method.

(Preparation method)

The following ingredients were dissolved or dispersed one after another in purified water at room temperature to obtain the samples.

TABLE 5

| | Reference test | Example 10 | Example 11 | Example 12 | Comparative example 1 | Comparative example 2 |
|---|---|---|---|---|---|---|
| [Formulation (I)] | | | | | | |
| Isostearyl alcohol (Emery type) | — | 1.0 | 5.0 | 50.0 | — | — |
| Benzyl alcohol | — | — | — | — | 5.0 | — |
| n-stearyl alcohol | — | — | — | — | — | 5.0 |
| Paraphenylenediamine | 0.5 | 0.5 | 0.5 | 0.5 | 0.5 | 0.5 |
| Sodium hydrosulfite | Appropriate amount | Appropriate amount | Appropriate amount | Appropriate amount | Appropriate amount | Appropriate amount |
| L-ascorbic acid | Appropriate amount | Appropriate amount | Appropriate amount | Appropriate amount | Appropriate amount | Appropriate amount |
| EDTA salt | Appropriate amount | Appropriate amount | Appropriate amount | Appropriate amount | Appropriate amount | Appropriate amount |
| Monoethanolamine | Adjust to pH 10 | Adjust to pH 10 | Adjust to pH 10 | Adjust to pH 10 | Adjust to pH 10 | Adjust to pH 10 |
| Purified water | Balance | Balance | Balance | Balance | Balance | Balance |
| [Formulation (II)] | | | | | | |
| Aqueous hydrogen | 18.0 | 18.0 | 18.0 | 18.0 | 18.0 | 18.0 |

TABLE 5-continued

|  | Reference test | Example 10 | Example 11 | Example 12 | Comparative example 1 | Comparative example 2 |
|---|---|---|---|---|---|---|
| peroxide (30%) |  |  |  |  |  |  |
| Sodium stannate | Appropriate amount | Appropriate amount | Appropriate amount | Appropriate amount | Appropriate amount | Appropriate amount |
| Methyl parabane | Appropriate amount | Appropriate amount | Appropriate amount | Appropriate amount | Appropriate amount | Appropriate amount |
| Phosphate buffer | Adjust to pH 3.5 | Adjust to pH 3.5 | Adjust to pH 3.5 | Adjust to pH 3.5 | Adjust to pH 3.5 | Adjust to pH 3.5 |
| Purified water | Balance | Balance | Balance | Balance | Balance | Balance |
| Dyeing test | Reference | ⊚ | ⊚ | ⊚ | Δ | X |

As shown in Table 5, each of the oxidation hair dye compositions containing isostearyl alcohol has a superior hair dyeing effect compared with the reference test sample.

Samples were obtained using the recipes of the following Examples 13–16. Each of them was a oxidation hair dye composition with an excellent hair dyeing effect.

Example 13

[Formulation (I)]

| Isostearyl alcohol (Emery type) | 10.0 |
| Paraphenylenediamine | 0.5 |
| Aqueous ammonia (28%) | Adjust to pH 10.0 |
| L-ascorbic acid | Appropriate amount |
| Sodium hydrosulfite | Appropriate amount |
| EDTA salt | Appropriate amount |
| Purified water | Balance |

[Formulation (II)]

| Aqueous hydrogen peroxide (30%) | 18.0 |
| Sodium stannate | Appropriate amount |
| Methylparabane | Appropriate amount |
| Phosphate buffer | Adjust to pH 3.5 |
| Purified water | Balance |

(Preparation method)

The ingredients listed above were dissolved or dispersed one after another in purified water at room temperature to obtain the samples.

Example 14

[Formulation (I)]

| Isostearyl alcohol (PK type) | 10.0 |
| Paraphenylenediamine | 0.5 |
| Aqueous ammonia | Adjust to pH 10.0 |
| L-ascorbic acid | Appropriate amount |
| Sodium hydrosulfite | Appropriate amount |
| EDTA salt | Appropriate amount |
| Purified water | Balance |

[Formulation (II)]

| Aqueous hydrogen peroxide (30%) | 18.0 |
| Sodium stannate | Appropriate amount |
| Methylparabane | Appropriate amount |
| Phosphate buffer | Adjust to pH 3.5 |
| Purified water | Balance |

(Preparation method)

The ingredients listed above were dissolved or dispersed one after another in purified water at room temperature to obtain the samples.

Example 15

[Formulation (I)]

| Isostearyl alcohol | 10.0 |
| Squalane | 5.0 |
| Paraphenylenediamine | 0.5 |
| Aqueous ammonia | Adjust to pH 10.0 |
| L-ascorbic acid | Appropriate amount |
| Sodium hydrosulfite | Appropriate amount |
| EDTA salt | Appropriate amount |
| Purified water | Balance |

[Formulation (II)]

| Aqueous hydrogen peroxide (30%) | 18.0 |
| Sodium stannate | Appropriate amount |
| Methylparabane | Appropriate amount |
| Phosphate buffer | Adjust to pH 3.5 |
| Purified water | Balance |

(Preparation method)

The ingredients listed above were dissolved or dispersed one after another in purified water at room temperature to obtain the samples.

Example 16

[Formulation (I)]

| Isostearyl alcohol | 10.0 |
| Methylphenylpolysiloxane | 5.0 |
| Paraphenylenediamine | 0.5 |
| Aqueous ammonia | Adjust to pH 10.0 |
| L-ascorbic acid | Appropriate amount |
| Sodium hydrosulfite | Appropriate amount |
| EDTA salt | Appropriate amount |
| Ion-exchanged water | Balance |

[Formulation (II)]

| Aqueous hydrogen peroxide (30%) | 18.0 |
| Sodium stannate | Appropriate amount |
| Methylparabane | Appropriate amount |
| Phosphate buffer | Adjust to pH 3.5 |
| Ion-exchanged water | Balance |

(Preparation method)

The ingredients listed above were dissolved or dispersed one after another in ion-exchanged water at room temperature to obtain the samples. The 2-formulation type oxidation hair dye described above had an excellent hair dyeing effect.

What is claimed is:

1. An emulsion for hair treatment comprising a formulation (I) which is a water-in-oil emulsion and contains a main agent selected from the group consisting of a hair dye, a hair bleach, a permanent wave agent and a depilatory in the water phase, and a formulation (II) which, when mixed with said formulation (I), causes a phase inversion of said formulation (I) into an oil-in-water emulsion and/or causes demulsification of said formulation (I).

2. The emulsion for hair treatment of claim 1 wherein polar oil is contained in the oil phase of said formulation (I).

3. The emulsion for hair treatment of claim 2 wherein the aforementioned polar oil is a higher alcohol or ester oil which is in a liquid state at ambient temperatures.

4. The emulsion for hair treatment of claim 2 wherein the aforementioned polar oil is isostearyl alcohol.

5. The emulsion for hair treatment of claim 1 wherein aforementioned formulation (I) also contains a water soluble polymer compound.

6. The emulsion for hair treatment of claim 5 wherein the aforementioned water soluble polymer compound is selected from the group consisting of carboxymethyl cellulose, hydroxyethyl cellulose, hydroxypropyl cellulose and cationized cellulose and mixtures thereof.

7. The emulsion for hair treatment of claim 1, wherein formulation (II) contains a destabilizing agent selected from the group consisting of a lower alcohol, an inorganic salt and a hydrophilic surfactant with an HLB value of 12 or more.

8. An emulsion for hair treatment comprising a formulation (I) which is a water-in-oil emulsion and contains a main agent comprising an oxidation dye in the water phase and an oil soluble polymer compound in the oil phase, and a formulation (II) which, when mixed with said formulation (I), causes a phase inversion of said formulation (I) into an oil-in-water emulsion and/or causes demulsification of said formulation (I), said formulation (II) containing an oxidizing agent and said emulsion for hair treatment is an oxidation hair dye.

9. The emulsion for hair treatment of claim 8 wherein polar oil is contained in the oil phase of said formulation (I).

10. The emulsion for hair treatment of claim 8 wherein the aforementioned oil soluble polymer compound is a single cellulose ether or a mixture thereof.

11. The emulsion for hair treatment of claim 10 wherein the aforementioned cellulose ether is ethyl cellulose.

12. The emulsion for hair treatment of claim 9 wherein the aforementioned polar oil is a higher alcohol or ester oil which is in a liquid state at ordinary temperatures.

13. The emulsion for hair treatment of claim 9 wherein the aforementioned polar oil is isostearyl alcohol.

14. An oxidation hair dye comprising a formulation (I) which is a water-in-oil emulsion and contains an oxidation dye in the water phase and ethyl cellulose and isostearyl alcohol in the oil phase, and a formulation (II) which, when mixed with said formulation (I), causes a phase inversion of said formulation (I) into an oil-in-water emulsion and/or causes demulsification of said formulation (I).

* * * * *